(12) United States Patent
Sater

(10) Patent No.: US 7,427,288 B2
(45) Date of Patent: Sep. 23, 2008

(54) MECHANICALLY EXPANDABLE DISTAL PROTECTION APPARATUS AND METHOD OF USE

(75) Inventor: Ghaleb A. Sater, Acton, MA (US)

(73) Assignee: Medtronic Vascular, Inc., Santa Rose, CA (US)

(*) Notice: Subject to any disclaimer, the term of this patent is extended or adjusted under 35 U.S.C. 154(b) by 478 days.

(21) Appl. No.: 11/148,718

(22) Filed: Jun. 9, 2005

(65) Prior Publication Data

US 2006/0282113 A1    Dec. 14, 2006

(51) Int. Cl.
*A61M 29/00*    (2006.01)

(52) U.S. Cl. ........................ 606/200; 606/194
(58) Field of Classification Search ......... 600/184–200; 606/106–236; 623/17.11, 17.16; 604/104–107
See application file for complete search history.

(56) References Cited

U.S. PATENT DOCUMENTS

| | | | | |
|---|---|---|---|---|
| 4,832,055 A * | 5/1989 | Palestrant | ................... | 128/899 |
| 5,370,657 A * | 12/1994 | Irie | ............................ | 606/200 |
| 5,827,324 A | 10/1998 | Cassell et al. | | |
| 6,030,406 A * | 2/2000 | Davis et al. | .................. | 606/198 |
| 6,129,762 A | 10/2000 | Li | | |
| 6,302,893 B1 * | 10/2001 | Limon et al. | ................. | 606/108 |
| 6,306,163 B1 * | 10/2001 | Fitz | ............................ | 623/1.12 |
| 6,569,184 B2 * | 5/2003 | Huter | ........................ | 606/200 |
| 6,663,652 B2 | 12/2003 | Daniel et al. | | |
| 2002/0099407 A1 | 7/2002 | Becker et al. | | |
| 2003/0105484 A1 * | 6/2003 | Boyle et al. | .................. | 606/200 |
| 2003/0130681 A1 | 7/2003 | Ungs | | |
| 2003/0130682 A1 | 7/2003 | Broome et al. | | |
| 2003/0135232 A1 | 7/2003 | Douk et al. | | |
| 2003/0208225 A1 | 11/2003 | Goll et al. | | |
| 2003/0225418 A1 | 12/2003 | Esksuri et al. | | |
| 2004/0077999 A1 * | 4/2004 | Selmon et al. | ............. | 604/104 |
| 2004/0167568 A1 * | 8/2004 | Boyle et al. | .................. | 606/200 |
| 2004/0260331 A1 * | 12/2004 | D'Aquanni et al. | ......... | 606/200 |
| 2004/0267301 A1 * | 12/2004 | Boylan et al. | ................ | 606/200 |
| 2005/0177106 A1 * | 8/2005 | Naimark et al. | ............. | 604/104 |
| 2006/0052814 A1 * | 3/2006 | Sater | .......................... | 606/200 |

* cited by examiner

*Primary Examiner*—(Jackie) Tan-Uyen Ho
*Assistant Examiner*—Erin Colello

(57) ABSTRACT

An embolic protection apparatus having a deflector tube and two expanders each having a plurality of circumferentially spaced, longitudinally oriented fingers. The fingers of each expander have radially constrained ends and radially expandable ends aligned opposite the fingers of the other expander. The deflector tube is disposed within one of the expanders that also has a flexible sleeve covering at least the fingers of the expander. The deflector and the expanders are engageable with each other using compound leverage to transform the apparatus between a collapsed configuration and an expanded configuration wherein the fingers of the covered expander are radially splayed to dilate the sleeve. Also disclosed are a catheter having the protection apparatus and a method of using the catheter.

20 Claims, 5 Drawing Sheets

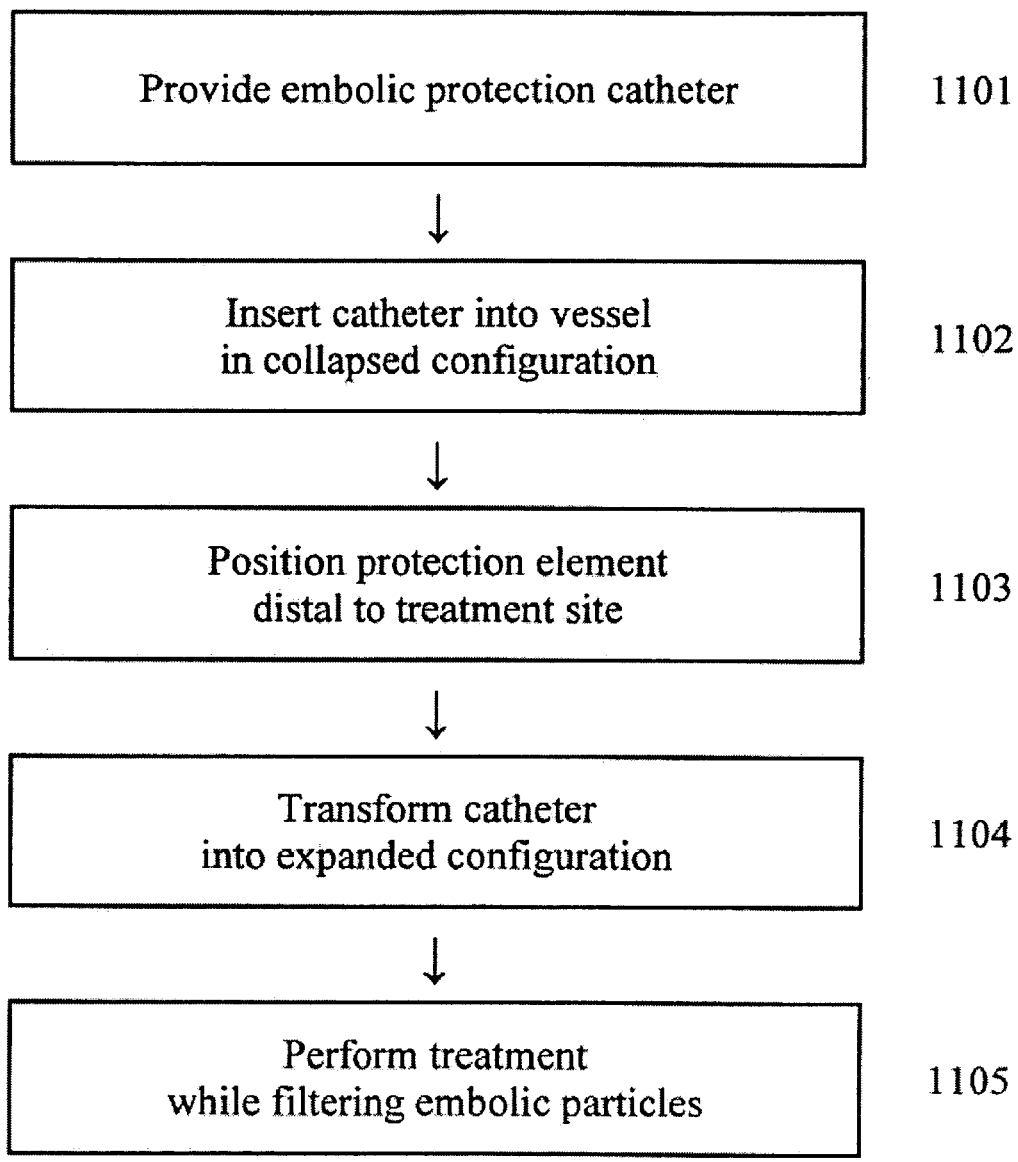

MECHANICALLY EXPANDABLE DISTAL PROTECTION APPARATUS AND METHOD OF USE

FIELD OF THE INVENTION

The present invention relates generally to intraluminal devices for capturing particulates in a vessel of a patient. More particularly, the invention relates to filters or occluders for capturing emboli in a vessel during an interventional vascular procedure. Furthermore, the invention concerns a distal protection apparatus mounted on a guidewire that can also be used to direct an interventional catheter to a treatment site within a patient.

BACKGROUND OF THE INVENTION

Various intervention techniques have been developed to treat narrowings in blood vessels, allowing increased blood flow through the vessels. One technique for treating stenosis or occlusion of a blood vessel is balloon dilatation, or percutaneous transluminal angioplasty (PTA). Generally, an arterial sheath is introduced through a puncture or incision in the patient's skin to provide percutaneous access to blood vessels. This is followed by insertion of a balloon catheter through the arterial sheath and its advancement through the blood vessels to the target site, where the stenosis is then dilated. PTA catheters are commonly guided through blood vessels by thin wires called guidewires, which may be either solid or hollow. To provide radial support to the treated vessel in order to prolong the positive effects of PTA, a stent may be implanted in conjunction with the procedure.

Thrombectomy is a minimally invasive technique for removal of an entire thrombus or a sufficient portion of the thrombus to enlarge the stenotic or diseased blood vessel and may be accomplished instead of a PTA procedure. Atherectomy is another well-known minimally invasive procedure that mechanically cuts or abrades a stenosis within the diseased portion of the vessel. Alternatively, ablation therapies use laser or RF signals to superheat or vaporize a thrombus within the vessel.

During each of these procedures, there is a risk that emboli dislodged by the procedure will migrate through the circulatory system and cause ischaemic events, such as infarction or stroke. Thus, clinicians have approached prevention of escaped emboli through use of occlusion devices, filters, lysing, and aspiration techniques. For example, it is known to remove the embolic material by suction through an aspiration lumen in the treatment catheter or by capturing emboli in a filter or occlusion device positioned distal of the treatment area. The terms "distal" and "proximal" are used herein with respect to the treating clinician: Distal or distally refer to elements distant from, or a direction away from the clinician, and proximal or proximally, refer to elements closer to, or a direction towards the clinician.

A difficulty associated with combing angioplasty with embolic protection is the limited time available to perform the procedure. That is, in order to contain emboli produced during intravascular therapy, the vessel may be occluded, meaning that no blood perfuses through the vessel to the end organ. Thus, depending upon the patient's vasculature and the organ involved, the complete procedure may need to be completed within just a few minutes.

Known embolic protection guidewires comprise an inflatable occlusion balloon located adjacent the distal end of a hollow guidewire. Dilute radiopaque contrast liquid is forced through the guidewire lumen to inflate and deflate the occlusion balloon. However, operating the balloon may take longer than desired due to the viscosity of the inflation medium, the small size of the inflation lumen, and the requirement to attach, detach and operate one or more inflation accessories at the proximal end of the guidewire.

U.S. Pat. No. 6,312,407 B1 teaches mechanically operated occlusion devices that may function more quickly than occlusion balloons, thus saving time during the treatment procedure. However, some mechanical occluder designs are complex and costly to produce.

Another known type of embolic protection guidewire comprises a filter located adjacent the distal end of the guidewire. A filter guidewire may include a slidable sheath to restrain a self-expanding filter during delivery and retrieval of the device. Alternatively, a filter apparatus may be mechanically expandable and collapsible, using push-pull operation of coaxially sliding inner and outer shafts to translocate the ends of the filter. However, known filter arrangements may be complex to make or operate, or they may have an undesirably large collapsed profile, which can limit the filter's ability to cross tight stenoses. Accordingly, there is a need for a simplified, low-profile embolic protection device.

SUMMARY OF THE INVENTION

The present invention provides an embolic protection apparatus having a deflector tube and two expanders each having a plurality of circumferentially spaced, longitudinally oriented fingers. The fingers of each expander have radially constrained ends and radially expandable ends aligned opposite the fingers of the other expander. The deflector tube is disposed within one of the expanders that also has a flexible sleeve covering at least the fingers of the expander. The deflector and the expanders are engageable with each other using compound leverage to transform the apparatus between a collapsed configuration and an expanded configuration wherein the fingers of the covered expander are radially splayed to dilate the sleeve. Also disclosed are a catheter having the protection apparatus and a method of using the catheter.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof. The accompanying drawings are not to scale.

BRIEF DESCRIPTION OF THE DRAWINGS

FIG. 11 schematically illustrates a method of using an embolic protection device in accordance with the invention.

DETAILED DESCRIPTION OF THE INVENTION

Figure 1:
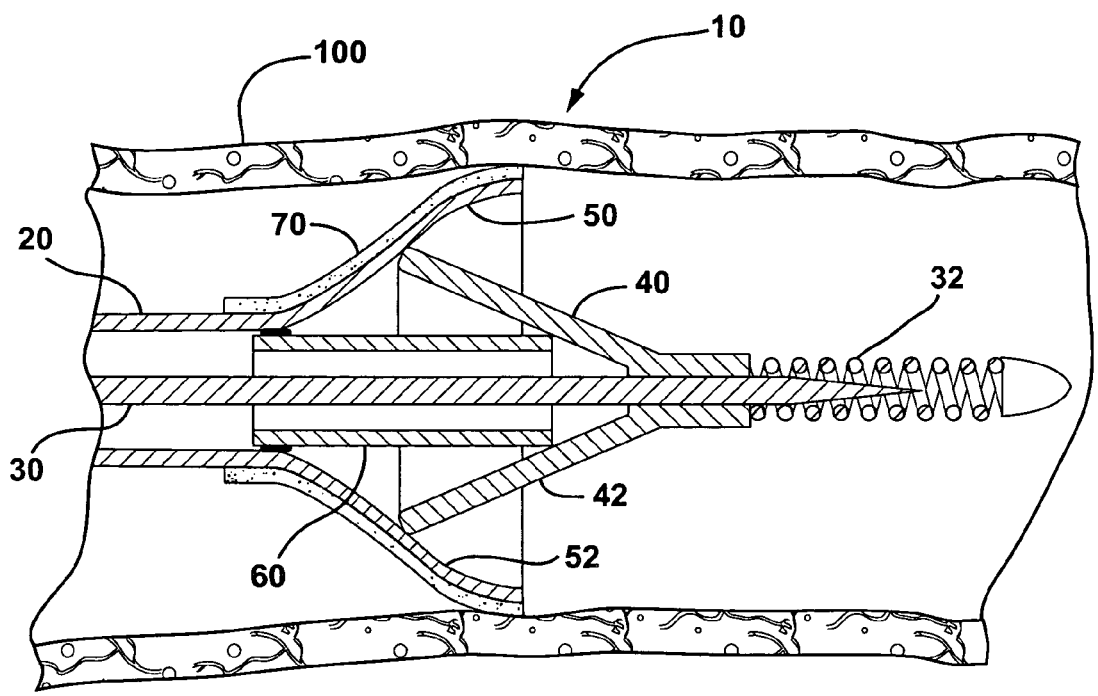
FIG. 1 illustrates a side view of a distal portion of an embolic protection guidewire in accordance with the invention, shown in the expanded configuration and partially sectioned for clarity.

Although the following description of the invention relates to the capture of embolic material that may be dislodged during vascular interventions, it is to be understood that the invention is applicable to other procedures in which the user desires to occlude or filter fluid flowing through a tubular body vessel, either temporarily or permanently. In FIG. 1, embolic protection guidewire 10 includes outer tube 20 and inner shaft 30 that extends slidably through and extends from outer tube 20. Flexible tubular tip member 32, such as a coil spring, is fixed around the tapered distal end of inner shaft 30.

Distal expander 40 is coupled to inner shaft 30, and has a tubular body with a plurality of fingers 42 that are longitudinally oriented and circumferentially spaced about the proximal end of expander 40. Fingers 42 have radially expandable proximal ends or tips, and radially constrained distal ends that are formed as an integral proximal portion of the tubular body of distal expander 40. Proximal expander 50 comprises a plurality of fingers 52 that are longitudinally oriented and circumferentially spaced about, and formed as an integral distal portion of, outer tube 20. Fingers 52 have radially expandable distal ends or tips, and radially constrained proximal ends. The proximal and distal expanders are longitudinally aligned in a slidable, opposed, mating arrangement such that fingers 52 are aligned with fingers 42.

Figure 2:
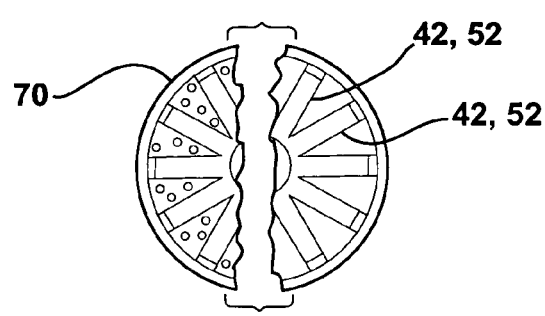
FIG. 2 illustrates an end view of a sleeve-covered expander in accordance with the invention.

Deflector tube 60 is disposed within proximal expander 50 and has a tube proximal end coupled to outer tube 20. Inner shaft 30 slides within deflector tube 60. Sleeve 70 is mounted about proximal expander 50 to cover at least fingers 52. Sleeve 70 may be porous, as shown on the left side of FIG. 2, for use as a filtration membrane. Alternatively, sleeve 70 may be non-porous, as shown on the right side of FIG. 2, for use as an occlusion membrane.

Figure 3:
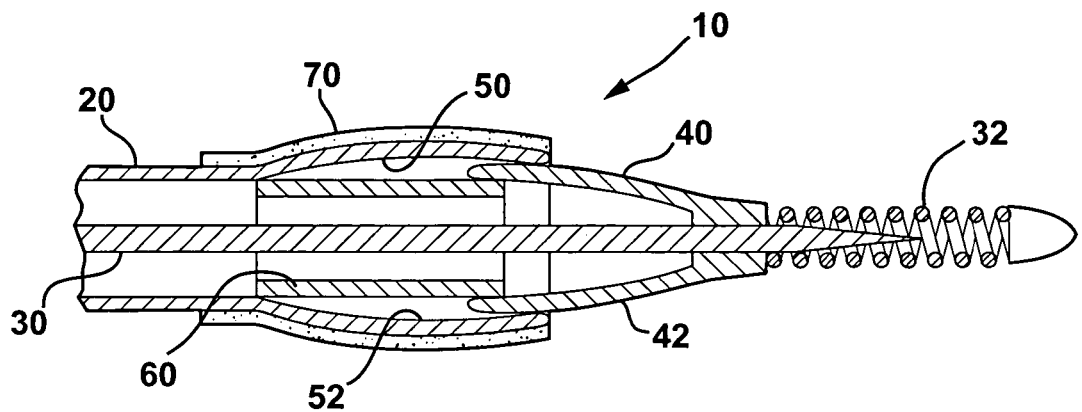
FIG. 3 illustrates a side view of the invention of FIG. 1, shown in a partially collapsed configuration and partially sectioned for clarity.

Relative longitudinal movement between distal expander 40 and deflector tube 60, and between the proximal and distal expanders, accompanies a transformation of embolic protection guidewire 10 between an expanded configuration, as shown in FIG. 1, and a collapsed configuration shown in FIG. 3. The operative longitudinal movement between the three components is achieved by pulling or pushing outer tube 20 with respect to inner shaft 30. Such action may be accomplished, if desired, by use of a removable accessory handle (not shown) that grips and manipulates proximal portions of outer tube 20 and inner shaft 30 outside the patient. Sliding distal expander 40 and deflector tube 60 toward each other forces fingers 42 to spread or splay radially outward about deflector tube 60. Sliding proximal expander 50 and distal expander 40 toward each other forces fingers 52 to splay radially outward about splayed fingers 42, thus dilating sleeve 70 into sealing engagement with the inner wall of patient's vessel 100.

The mechanical interaction of distal expander 40, proximal expander 50, and deflector tube 60 manipulates corresponding fingers 42, 52 like compound levers to dilate sleeve 70 into sealing apposition with the inner wall of vessel 100. By definition, third-class levers have the "effort" placed between the "load" and the "fulcrum," and compound levers combine two or more levers. In a first set of compound levers of the invention, sliding distal expander 40 and deflector tube 60 toward each other causes fingers 42 to be splayed open like third class levers wherein the distal end of distal expander 40 is fixed to inner shaft 30 to define a "fulcrum" for each of fingers 42, the "loads" are defined where the proximal ends of fingers 42 contact fingers 52, and the "effort" is applied between the proximal and distal ends of fingers 42 by the distal end of deflector tube 60.

In a second set of compound levers of the invention, sliding proximal expander 50 and distal expander 40 toward each other causes fingers 52 to also be splayed open like third class levers wherein the proximal end of proximal expander 50 is fixed to outer tube 20 to define a "fulcrum" for each of fingers 52, the "loads" are defined where the distal ends of fingers 52 contact the inner wall of vessel 100 through sleeve 70, and the "effort" is applied between the proximal and distal ends of fingers 52 by the distal ends of fingers 42. Thus, the first and second sets of levers interact as compound levers such that the radial distances traveled by the distal ends of fingers 52 are multiples of the relative longitudinal distances traveled by the distal expander 40, proximal expander 50, and deflector tube 60.

Figure 4:
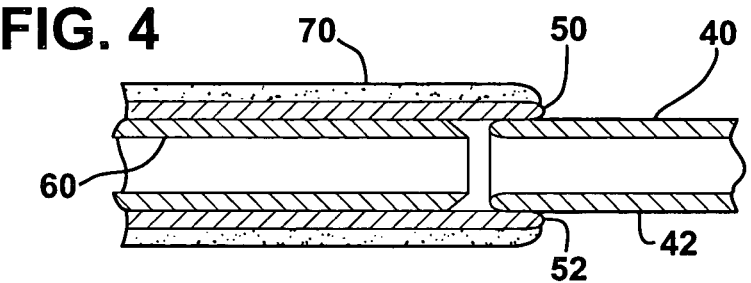
FIGS. 4-6 illustrate various collapsed configurations of the deflector tube and expanders in accordance with the invention.
Figure 5:
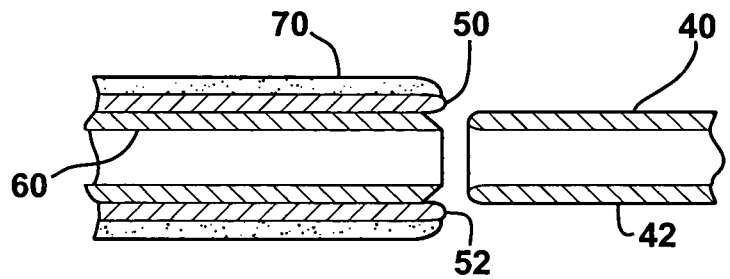
Figure 6:
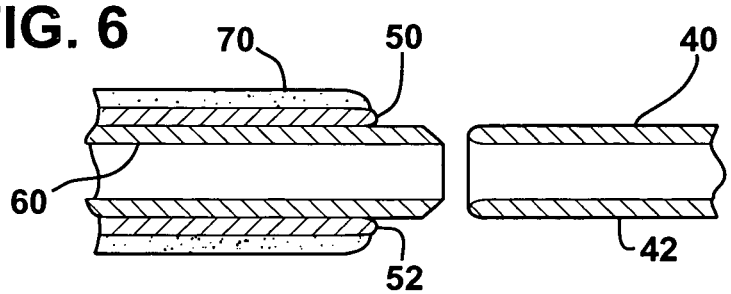

In the collapsed configuration shown in FIG. 3, the proximal ends of fingers 42 are disposed between proximal expander 50 and deflector tube 60. This arrangement advantageously ensures that fingers 42 are already disposed between proximal expander 50 and deflector tube 60 to easily begin the required sliding motion to expand and dilate sleeve 70 as described above. However, this arrangement has the disadvantage of an unnecessarily large collapsed profile. FIGS. 4-6 show alternative collapsed configuration arrangements of fingers 42, proximal expander 50 and deflector tube 60. In each of FIGS. 4-6, fingers 42 are not disposed between proximal expander 50 and deflector tube 60 such that the collapsed profile of the configuration is smaller than that shown in FIG. 3.

As shown in FIG. 4, proximal expander 50 extends beyond deflector tube 60, such that the proximal tips of fingers 42 are disposed within proximal expander 50 and may abut deflector tube 60. To begin expansion of embolic protection guidewire 10, the ends of fingers 42 need to overcome an initial step onto deflector tube 60 and begin sliding toward the expanded configuration. To facilitate this movement, the distal end of deflector tube 60 may include a radius, a tapered ramp or a chamfer. The proximal ends of fingers 42 may be rounded or chamfered to aid in overcoming the initial step and/or to aid the insertion of fingers 42 between proximal expander 50 and deflector tube 60 when a clinician begins to expand the embolic protection device. As shown in FIG. 5, proximal expander 50 ends approximately flush with the distal end of deflector tube 60. As shown in FIG. 6, proximal expander 50 ends proximally of the distal end of deflector tube 60. The different arrangements shown in FIGS. 4-6 have different proportions that can create different compound leverage for embolic protection guidewire 10. Sliding the proximal and distal expanders apart allows embolic protection guidewire 10 to return to the collapsed configuration.

Embolic protection guidewire 10 may be sized for directing catheters to a targeted treatment location. For example, outer tube 20 may be thin walled tubing having an outer diameter of 0.014 in (0.0006 mm) for directing catheters in coronary or cerebral arteries, or in other small caliber vessels. Treatments in larger target vessels may require outer tube 20 to have a larger outer diameter for guiding relatively larger therapy catheters. Outer tube 20 may be formed of metals such as stainless steel or TiNi (nitinol) or of a high modulus polymer such as thermoset polyimide. Inner shaft 30 may be a solid core wire or a combination of tubing and wire made of a metal such as stainless steel or TiNi (nitinol).

Figure 7:
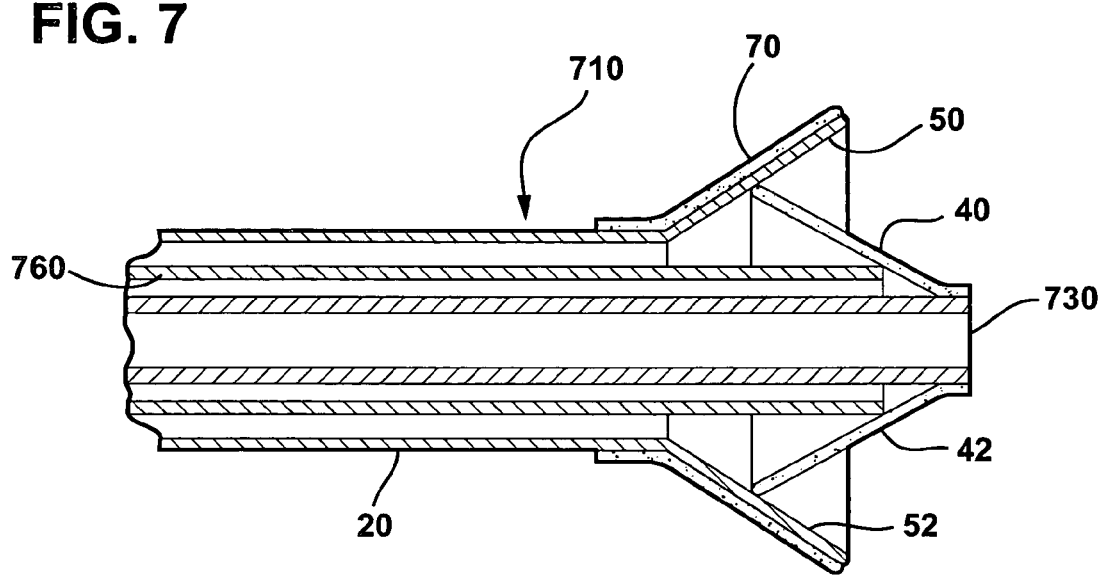
FIG. 7 illustrates a side view of a distal portion of another embolic protection device in accordance with the invention, shown in the expanded configuration and partially sectioned for clarity.

FIG. 7 shows embolic protection catheter 710, which is similar to embolic protection guidewire 10, except that inner shaft 730 is a hollow tube having a guidewire lumen there through. Deflector tube 760 is also different from deflector tube 60 in that tube 760 is long enough to extend through outer tube 20. Deflector tube 760 slides freely over inner shaft 730, and slides freely within outer tube 20. In this embodiment of the invention, all three components, outer tube 20, deflector tube 760, and inner shaft 730 can be manipulated separately from outside the patient's body to effect different compound leverages or stepwise expansion of the embolic protection device. As with embolic protection guidewire 10, such action may be accomplished, if desired, by use of a removable accessory handle (not shown) that grips and manipulates proximal portions of outer tube 20, deflector tube 760 and inner shaft 730 outside the patient.

Figure 8:
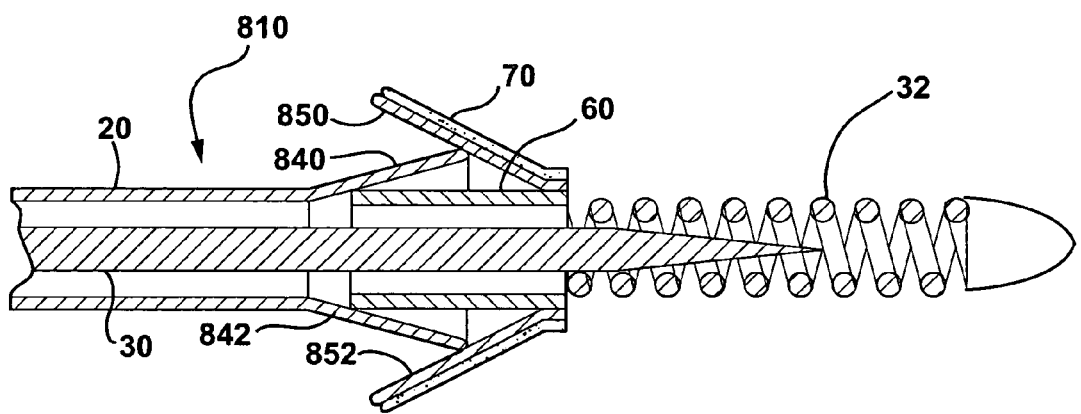
FIG. 8 illustrates a side view of a distal portion of yet another embolic protection device in accordance with the invention, shown in the expanded configuration and partially sectioned for clarity.

FIG. 8 shows embolic protection guidewire 810, which is similar to embolic protection guidewire 10, except that the positions and orientations of the expanders and the deflection tube are reversed. Deflector tube 60 is fixedly or slidingly disposed about inner shaft 30 adjacent tip member 32. Outer expander 850 has distal ends attached to the distal end of deflector tube 60. Inner expander 840 is formed as an integral distal portion of outer tube 20. Expanders 840, 850 and deflection tube 60 interact as compound levers, as described above, to dilate sleeve 70 into sealing apposition with the inner wall of vessel 100. Deflector tube 60 may abut tip member 32 to be restrained from sliding distally along inner shaft 30. When embolic protection guidewire 810 is in the expanded configuration, outer expander 850 has a proximally-facing frusto-conical shape such that embolic debris may be collected within expander 850 and sleeve 70. Transformation of guidewire 810 to the collapsed configuration can retain the collected embolic debris for removal with guidewire 810. Since the proximal and distal positions of the expanders and deflector tube 60 may be reversed, as discussed above, then the proximal and distal ends of these components, and the fingers, may be referred to as first and second ends.

In the expanded configuration, sleeve 70 can occlude fluid flow if it is formed of non-porous material, or sleeve 70 can filter fluid flow if it is formed of porous material. Sleeve 70 may be made from a natural rubber, a synthetic rubber, a thermoplastic elastomer, a styrenic thermoplastic elastomer, a styrene-butylene-styrene, an inelastic thermoplastic, a polyester, a polyamide, co-polymer, a blend, a lamination, or a combination of the above materials. Sleeve 70 may be made of an elastic material and fitted snugly about collapsed proximal expander 50 to provide a low crossing profile. Sleeve 70 may also be made of an inelastic material and folded about the collapsed expander 50 similar to a deflated angioplasty balloon. Sleeve 70 is adhered, at its distal and proximal ends, to embolic protection guidewire 10, 710. Sleeve 70 ensures that spaces between fingers 52, 852 are covered to prevent leakage of potentially contaminated fluid there through when expander 50 is expanded. Sleeve 70 may be bonded to the underlying portions of guidewire 10, 710 using known adhesives and techniques. The distal end of Sleeve 70 may be attached to the distal ends of fingers 52.

Figure 9:
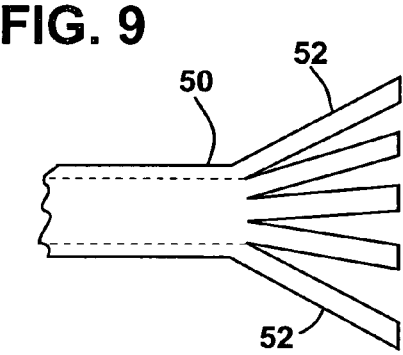
FIG. 9 illustrates an integrally-formed expander in accordance with the invention.
Figure 10:
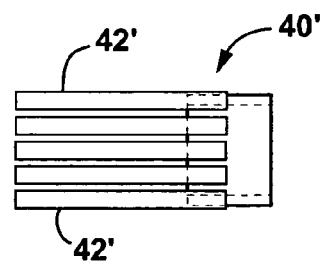
FIG. 10 illustrates an assembled expander in accordance with the invention.

As shown in FIG. 9, integrally formed expander 50 may be cut from stainless steel, TiNi or other metal tubing using known techniques such as laser machining or electrical discharge machining (EDM). Alternatively, expander 50 may be cut from a flat metal sheet, then rolled up and joined at the edges to form a tube. Alternatively, FIG. 10 illustrates expander 40' formed by attaching separately formed fingers 42' to a tubular body, as by welding, soldering, or gluing. Fingers 42 and 42' are shown with parallel sides, but alternative finger shapes may also be useful. Expanders 40, 740, 840 and 50, 750, 850 can be formed from any of the above mentioned techniques.

Deflector tube 60, 760 may be formed from a seamless tube or from a flat sheet of material that is rolled up and bonded to form a tube. A variety of biocompatible incompressible materials may be used to fabricate deflector tube 60, 760 including metals and plastics. As illustrated in FIGS. 4-6, deflector tube 60, 760 may have a chamfer on one end to receive and guide the tips of fingers up a first step in diameter as expander 40, 740, 840 and tube 60, 760 are slid against each other.

FIG. 11 schematically illustrates a method of using an embolic protection catheter, as follows. First, an embolic protection catheter is provided, such as filter guidewire 10 or 810 (step 1101). The filter guidewire is inserted into the patient's vessel with the filter in the collapsed configuration (step 1102). The filter guidewire is navigated through the vessel until the protection element, e.g. the filter, is positioned distal to an intended treatment site, such as a stenosis (step 1103). The protection element is transformed from the collapsed configuration to the expanded configuration such that sleeve 70 is sealingly apposed to the inner wall of the vessel (step 1104). A treatment, such as angioplasty and/or stent deployment, is performed on the stenosis, while sleeve 70 filters any embolic particles from fluid flowing there through (step 1105). In the case of a filter or occluder guidewire, the treatment catheter can be slid over the shaft of the indwelling guidewire. Trapped embolic debris may be aspirated before the filter is collapsed and the filter guidewire is removed from the patient. Similar methods may be performed using inventive catheters or guidewires having non-porous sleeve 70, to temporarily occlude the vessel and prevent downstream embolization.

It should be understood that the scope of the present invention is not to be limited by the illustrations for the foregoing description thereof, but rather by the appended claims, and certain variations and modifications of this invention will suggest themselves to one of ordinary skill in the art.

What is claimed is:

1. An embolic protection apparatus transformable between a collapsed configuration and a radially expanded configuration sealingly engageable with an inner wall of a tubular vessel of a human body, the apparatus comprising:
   an inner expander and an outer expander, each expander having a plurality of circumferentially spaced, longitudinally oriented fingers, the fingers of each expander being conjoined at a first end of the respective expander and being radially expandable at a second end of the respective expander, the expanders being aligned opposite each other such that, in the collapsed configuration, the second end of the inner expander is disposed adjacent the second end of the outer expander;
   a deflector tube disposed within the outer expander, the deflector tube having a distal end aligned with and disposed adjacent the second end of the inner expander in the collapsed configuration, wherein the distal end of the deflector tube contacts and slides along an inner surface of the fingers of the inner expander to radially expand the embolic protection apparatus; and
   a flexible sleeve mounted about at least the fingers of the outer expander.

2. The apparatus of claim 1, wherein in the expanded configuration, the fingers of the inner expander are radially splayed about the deflector tube.

3. The apparatus of claim 2, wherein the fingers of the inner expander contact and slide along an inner surface of the fingers of the outer expander to be slidably engageable therewith such that, in the expanded configuration, the fingers of the outer expander are radially splayed about the splayed fingers of the inner expander.

4. The apparatus of claim 1, wherein at least one of the expanders is formed integrally from a tube.

5. The apparatus of claim 1, wherein at least one of the expanders is formed as an assembly comprising a tube and a plurality of discrete fingers affixed thereto.

6. The apparatus of claim 1, wherein, in the collapsed configuration, the fingers of at least one of the expanders are juxtaposed with adjacent conjoined fingers.

7. The apparatus of claim 1, wherein the sleeve is non-porous such that the expanded configuration is capable of sealing against the wall of the vessel and occluding fluid flow there through.

8. The apparatus of claim 1, wherein the sleeve is porous such that the expanded configuration is capable of sealing against the wall of the vessel and filtering embolic particles from fluid flowing there through.

9. The apparatus of claim 1, wherein at least a proximal end of the deflector tube is fixed to and slidable with the outer expander.

10. An embolic protection catheter being capable of transformation between a collapsed configuration and an expanded configuration, the catheter comprising:
   an elongate outer tube having a distal end;
   an elongate inner shaft extending slidably through the outer tube and having a distal end;
   a distal expander having a plurality of circumferentially spaced, longitudinally oriented fingers, the fingers having radially expandable proximal ends and radially constrained distal ends coupled to the inner shaft adjacent the inner shaft distal end;
   a proximal expander having a plurality of circumferentially spaced, longitudinally oriented fingers, the fingers having radially expandable distal ends and radially constrained proximal ends coupled to the outer tube adjacent the outer tube distal end, the distal and proximal expanders being aligned opposite each other such that, in the collapsed configuration, the proximal ends of the fingers of the distal expander are disposed adjacent the distal ends of the fingers of the proximal expander;
   a deflector tube slidably disposed about the inner shaft and having a distal end disposed adjacent the distal ends of the fingers of the proximal expander in the collapsed configuration, wherein the distal end of the deflector tube contacts and slides along an inner surface of the fingers of the distal expander to radially expand the embolic protection catheter; and
   a flexible sleeve covering at least the fingers of the proximal expander.

11. The catheter of claim 10, wherein sliding the inner shaft proximally within the deflector tube engages the distal expander with the distal end of the deflector tube to radially splay the fingers of the distal expander.

12. The catheter of claim 11, wherein sliding the inner shaft proximally within the outer tube slidably engages the proximal ends of the fingers of the distal expander with the fingers of the proximal expander to splay the fingers of the proximal expander about the splaying fingers of the distal expander.

13. The catheter of claim 10, wherein the transformation between the collapsed configuration and the expanded configuration is effectuated by the distal and proximal expanders interacting with each other using compound leverage.

14. The catheter of claim 10, wherein the deflector tube is elongate and extends slidably through the outer tube.

15. The catheter of claim 10, wherein the proximal expander is an integral portion of the outer tube.

16. The catheter of claim 10, wherein the inner shaft is selected from a group consisting of a core wire, a hollow shaft and a combination thereof.

17. The catheter of claim 10, wherein the sleeve comprises a material selected from a group consisting of a porous material, a non-porous material, a natural rubber, a synthetic rubber, a thermoplastic elastomer, a styrenic thermoplastic elastomer, a styrene-butylene-styrene, an inelastic thermoplastic, a polyester, a polyamide, a polyolefin, and a block co-polymer, a blend, a lamination, and a combination of the above materials.

18. The catheter of claim 10, wherein the sleeve is non-porous such that the expanded configuration is capable of sealing against the wall of the vessel and occluding fluid flow there through.

19. The catheter of claim 10, wherein the sleeve is porous such that the expanded configuration is capable of sealing against the wall of the vessel and filtering embolic particles from fluid flowing there through.

20. A method of using an embolic protection catheter, the method comprising:
   providing the embolic protection catheter of claim 19;
   inserting the catheter into the vessel of the human body with the catheter in the collapsed configuration;
   positioning the protection element distal to a treatment site;
   transforming the catheter into the expanded configuration sealing against the inner wall of the vessel; and
   performing a treatment at the treatment site while filtering embolic particles from fluid flowing through the protection element.

* * * * *